United States Patent [19]

Vasseur et al.

[11] Patent Number: 4,831,867

[45] Date of Patent: May 23, 1989

[54] METHODS AND DEVICES FOR MEASURING THE RATIO OF INCONDENSABLES IN GAS MIXTURE

[76] Inventors: Jean Vasseur, 7 rue Brezin, 75014 Paris; Gilles Trystam, 7 Ave de la convention, 94110 Arcueil, both of France

[21] Appl. No.: 36,672

[22] PCT Filed: Jul. 23, 1986

[86] PCT No.: PCT/FR86/00263

§ 371 Date: Jun. 11, 1987

§ 102(e) Date: Jun. 11, 1987

[87] PCT Pub. No.: WO87/00631

PCT Pub. Date: Jan. 29, 1987

[30] Foreign Application Priority Data

Jul. 25, 1985 [FR] France .............................. 85 11652

[51] Int. Cl.⁴ ............................................ G01N 21/00
[52] U.S. Cl. .................................................... 73/29
[58] Field of Search ............................. 73/29, 861.41

[56] References Cited

U.S. PATENT DOCUMENTS

| 2,967,450 | 1/1961 | Shields et al. | 73/861.41 X |
| 4,507,875 | 4/1985 | Hirsch et al. | 73/29 X |
| 4,739,647 | 4/1988 | Monticelli, Jr. | 73/29 X |

FOREIGN PATENT DOCUMENTS

| 2846826 | 4/1980 | Fed. Rep. of Germany . |
| 3224506 | 7/1983 | Fed. Rep. of Germany . |
| 1085825 | 10/1967 | United Kingdom . |

*Primary Examiner*—Stewart J. Levy
*Assistant Examiner*—Joseph W. Roskos
*Attorney, Agent, or Firm*—Lee C. Robinson, Jr.

[57] ABSTRACT

A method and apparatus for measuring the ratio of incondensables in steam or other gaseous mixture. The mixture is led from a condenser through a transparent tube exposed to a light beam having a diameter approximately equal to the inside diameter of the tube, such that the beam is reflected by incondensable bubbles in the mixture but not by condensed droplets. A photoelectric sensor assembly is located in position to receive the light beam. The trajectory of the beam, and hence the signal from the sensor, is determined by whether the beam is intercepted by an incondensable bubble or a condensed droplet.

9 Claims, 3 Drawing Sheets

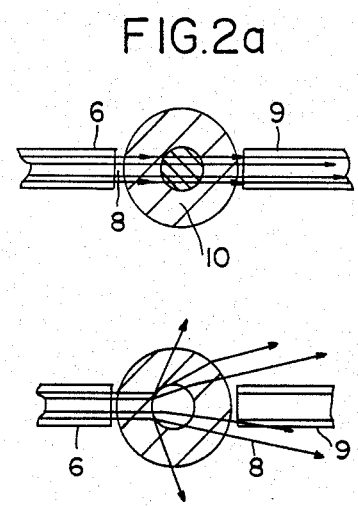
FIG.2a
FIG.2b
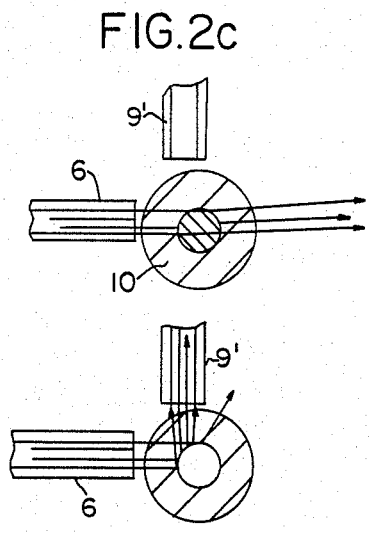
FIG.2c
FIG.2d
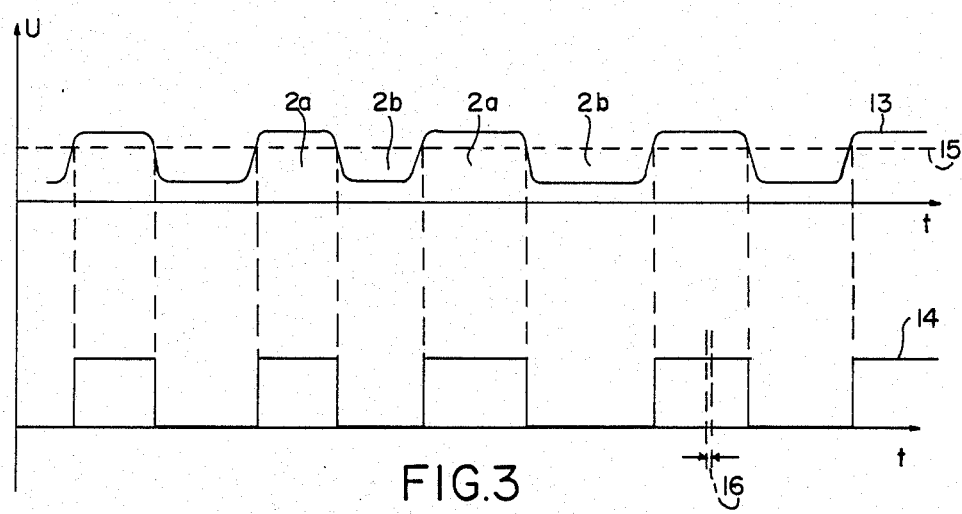
FIG.3

METHODS AND DEVICES FOR MEASURING THE RATIO OF INCONDENSABLES IN GAS MIXTURE

BACKGROUND OF THE INVENTION

The present invention is concerned with the measuring instruments and relates more particularly to a process and a device for measuring the content of uncondensable substances present in a gaseous mixture, especially steam considered as a heat-exchange fluid.

It will be recalled that the water intended for feeding boilers and coming from the distribution network generally undergoes two operations before it enters the boiler, namely passage through an ion-exchanger column for the purpose of demineralization, and thermal degassing; in spite of this degassing, a residual content of air remains in the water and appears again in the steam in the form of uncondensable substances. Another reason for the presence of air in the steam is that the pipelines and the vaporization or exchange vessel are bled insufficiently at the outset.

When steam is used as a heat-exchange fluid in an exchanger, the overall result of the presence of uncondensable substances in the steam is, on the one hand, a reduction in the heat flux between the steam and the exchange wall and, on the other hand, the occurrence of zones which are superheated in relation to other zones on the exchange wall.

These disadvantages attributable to the presence of uncondensable substances are usually overcome by means of periodic or continuous bleeding, that is to say the rejection of steam outside the exchanger; this bleeding is generally carried out systematically from time to time without any specific criterion, that is to say irrespective of the actual content of uncondensable substances in the steam; the result of this procedure is that either bleeding is insufficient and then gives rise to the above-mentioned disadvantages, or bleeding is too frequent and results in corresponding energy losses. Of course, the logical method is to bleed the system as a function of the content of uncondensable substances present in the steam, and this implies an evaluation of the content of the latter.

Two methods of measuring the content of uncondensable substances are known, both usually requiring a weighing operation; according to a first method, a representative portion of the gaseous mixture is extracted and condensed in a vessel containing cold water, underneath a measuring cylinder turned upside down in the form of a gasholder; after a certain time, the volume of gas collected is read off, the increase in the weight of water in the vessel attributable to the condensate is measured and the content of uncondensable substances is deduced from this; such a method is impractical, particularly because it is intermittent. A second method involves separately measuring, on the one hand, the instantaneous flowrate of the condensates by weighing and, on the other hand, the instantaneous flowrate of the uncondensable gases, for example by measuring the pressure in a vessel with gauged leakage, the ratio of these two flowrates giving the content of uncondensable substances; however, where low flowrates are concerned, particularly regarding gases, the latter method of measurement is especially inaccurate, above all for low contents of uncondensable substances.

SUMMARY

The object of the present invention is specifically to provide a process and devices for measuring the content of uncondensable substances, which process and devices are both convenient, accurate and continuous, require only a very low extraction rate and do not necessitate any manual involvement, but on the contrary can trigger bleeding operations automatically and under highly efficient control.

The originating idea of the present invention is based on the finding that, in a conduit of sufficiently small cross-section, the condensate and the uncondensable substances take the form of a succession of fractions of liquid and fractions of gas which are separated by meniscusses, these fractions being called respectively, for the sake of simplification, "drops" and "bubbles". The drops and bubbles have measurable lengths, and the ratio of the respective lengths on average is contant for a given content of uncondensable substances; moreover, this ratio of two lengths is largely independent of the speed of passage through the conduit, so that the extraction rate does not need to be known or constant from one minute to another or equal from one measuring channel to another where there is a plurality of measuring channels, and this simplifies the measurement considerably.

The measuring process according to the invention therefore involves evaluating the ratio between the lengths of the bubbles and those of the drops. This evaluation can be carried out in different ways, all arising from the invention, by utilizing the markedly different physical properties of bubbles and drops; as a nonlimiting indication, this evaluation can be made by weighing, by optical means, etc. It is the optical method which is the subject of a preferred development of the invention and of which exemplary embodiments are given below.

According to the present invention, a device for measuring the content of uncondensable substances present in a gaseous mixture is characterized, in general terms, in that it comprises, so as to act in combination, means for extracting at a constant rate a representative portion of the said gaseous mixture, and a condenser consisting of a tube of sufficiently small inside diameter to allow the isokinetic conveyance of the fractions of uncondensable substances, called bubbles, and the fractions of condensate, called drops, formed as a result of the condensation of the condensable substances in the said tube. The device also includes a transparent tube called a measuring tube or conduit of a cross-section substantially equal to or less than that of the condenser tube, the said measuring tube consisting of a material having a refractive index near that of the condensate, and an assembly comprising a light transmitter and a photoelectric receiver which are designed in such a way that the direction of the beam is substantially perpendicular to the axis of the measuring tube. The light flux of the beam is transmitted in a different way, depending on whether there is a bubble or a drop present inside the measuring tube in its path, and the receiver supplies a low voltage or a high voltage, depending on whether there is a bubble or a drop present in the path, thus clearly discriminating between the presence of a bubble or the presence of a drop in the path. By light is meant all the luminous radiations of the spectrum ranging from ultraviolet to infrared.

According to a first alternative embodiment, the light is generated in the form of a parallel light beam of substantially cylindrical cross-section comparable to the inner cross-section of the conduit of the measuring tube, so that the intersection of the transmitted beam and the conduit is approximately at a point, that is to say of small dimension in relation to the length of the drops; this alternative form of the device will be suitable more particularly for a numerical evaluation method which will be described later.

According to a second alternative embodiment, the measuring tube is straight and of such length that it contains a certain number of alternate drops and bubbles. The light beam has a highly flattened parallelipedic shape of a thickness substantially equal to the diameter of the conduit, the mid-plane of the beam merging with the axis of the measuring tube, so that the intersection of the beam and the conduit is approximately linear. This second alternative form of the device will be suitable more particularly for an analogue evaluation method which will be described later.

According to the present invention, the general process for measuring the content of uncondensable substances present in a gaseous mixture, the said process utilizing a device such as that described above in general terms, involves conveying the succession of bubbles and drops in the measuring tube at a substantially constant speed or even with a slow variation, and measuring optically the respective lengths of the bubbles and drops passing successively through the measuring tube. The content of uncondensable substances present in the gaseous mixture is deduced from the ratio between the length of the bubbles and the length of the drops.

According to the alternative numerical evaluation method, the lengths of the bubbles and drops are measured by measuring the time between the passages of the successive meniscusses separating the drops from the bubbles, at a given point on the measuring tube; preferably, the time measurement is made with reference to a clock, of which the period or time base is very small in relation to the passage time between two successive meniscusses.

The content of uncondensable substances can be evaluated from at least two of the measurements of the group of measurements which includes the cumulative measurement of the passage time of the drops: tg, the cumulative measurement of the passage time of the bubbles: tb, and the cumulative measurement of the passage time of the drops and bubbles: tt, these measurements being carried out on a reasonably numerous succession of drops and bubbles, taking into account one of the ratios of the group of ratios which includes tb/tg, tb/tt, tg/tt, tttg/tt. The total time can be counted over a predetermined number of alternations or over a predetermined period. In an alternative form of this second method, the "measuring-time preselection" time is called sliding, in the sense that the displayed value of the "tending" content of uncondensable substances is corrected on the basis of the most recent measurements made, at the same time as the oldest measurements are cancelled, microprocessor cards with a memory making it possible to do this easily; thus, there is no need to wait for the end of the preselected time in order to have the new "updated" value available.

According to the alternative analogue evaluation method, the ratio between the length of the bubbles and the length of the drops is deduced directly from the "optical weighing" of all the drops and bubbles present at the linear intersection of the beam and conduit.

The present invention will be understood from the following description of the general means and alternative operating methods of the process and devices of the invention, with reference to the Figures of the accompanying drawings, in which:

BRIEF DESCRIPTION OF THE DRAWINGS

FIGS. 2a to 2d illustrate diagrammatically, in a section through the conduit, the differential effects produced on the light beam as a result of transmission on the one hand (2a, 2b) and reflection on the other hand (2c, 2d), during the passage of a drop (2a, 2c) and during the passage of a bubble (2b, 2d), FIG. 3 is a graph showing the castellated formations of voltage which is unprocessed and then reshaped, representing the succession of "drops" and "bubbles"

DESCRIPTION OF CERTAIN PREFERRED EMBODIMENTS

Figure 1:
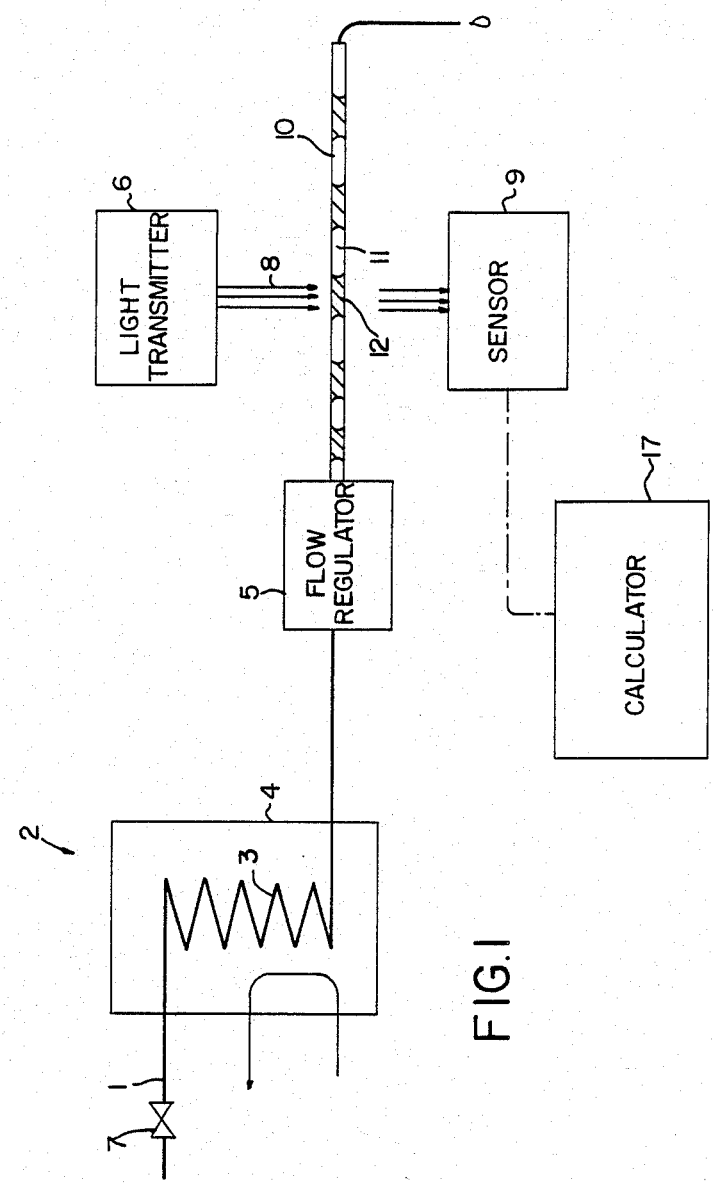
FIG. 1 is a general diagram of the means used by the invention.

In FIG. 1, a device for measuring the content of uncondensable substances comprises an extraction tube 1, a condenser 2 consisting of a coiled tube 3 and of a cooling-fluid vessel 4, flow-regulating means 5, such as a peristaltic pump, an assembly comprising a transmitter 6 for the beam 8 of parallel light and a photoelectric receiver 9, and a transparent measuring tube 10 having an inside diameter of 1 to 2 mm.

It will be noted that the flow-regulating means are optional, that if they are required they can also be located upstream of the condenser, and that they can consist of a simple valve 7, for example a needle valve, if steam under pressure relative to the atmosphere is to be extracted.

In the measuring tube 10 can be seen a succession of bubbles, such as 11, and drops, such as 12, separated from one another by meniscusses, the form of which depends on the type of material of which the measuring tube is made and on the type of condensate. In the illustrated embodiment the condensate is water and the material is glass. FIG. 1 shows an embodiment designed for the first alternative form, in which evaluation is based on the measurement of passage times; in this case, the beam 8 is cylindrical and of small diameter, and its intersection with the tube 10 is virtually at a point, that is to say only very small in relation to the length of the drops.

FIG. 2, which shows sections through a plane containing the beam 8 and perpendicular to the tube 10, illustrates the situation where a drop is located at the intersection of the conduit and the beam (FIG. 2a), and the situation where a bubble is located at this intersection (FIG. 2b). In the situation 2a, the beam 8 coming from the transmitter 6, for example by means of an optical fibre, is deflected only relatively slightly when it passes through the tube 10, because the refractive indices of water (n=1.33) and glass (n=1.5) are relatively near to one another; the beam is therefore intercepted virtually completely by the sensor 9 which is then excited; on the contrary, in situation 2b, the same beam is deflected appreciably because of the difference between the indices of glass and of the air (n=1) constituting the bubble, and the sensor 9 is excited only slightly.

FIGS. 2c and 2d illustrate how the sensor 9' is mounted with a receiving axis perpendicular to the beam transmission axis, and here the reflection effect will be used: when the beam meets a bubble (FIG. 2d) in the conduit, it is reflected towards the sensor which is then excited; if the beam meets a drop (FIG. 2c), it will be reflected only slightly towards the sensor 9' which will then be excited hardly at all. It is also possible to adopt a mounting arrangement comprising both a sensor mounted in the same way as 9 and a sensor mounted in the same way as 9'.

FIG. 3 shows by a graph 13 the electrical voltage u applied to the terminals of the cell of the sensor 9 and by the graph 14 a voltage rectified according to the crossing of the threshold 15 by the voltage of the preceding graph. The notches of the graph 14 therefore represent the succession in time of the drops and bubbles in the conduit, preferably according to the TTL standard (0 or 5 V d.c.). The process of the invention will then involve processing the signal of the graph 14 by measuring, with reference to a clock period 16, the duration of the notches representing water or air and then accumulating these respective periods to form the ratio from them and display a result.

These latter means, called calculator means, shown at 17 in FIG. 1 can assume two forms, depending on the method of calculation selected.

Figure 4:
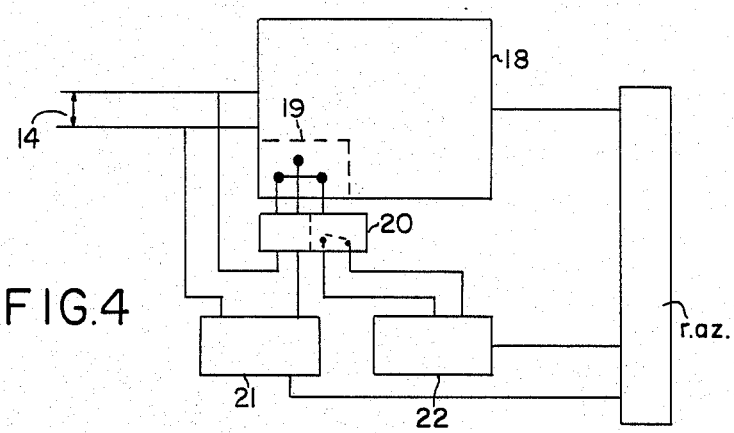
FIG. 4 is a general diagram of the means for evaluating the content of uncondensable substances according to a first method.

FIG. 4 shows the means for calculating by preselecting the number of "water pulses"; these means comprise a water-pulse counter 18 incorporating a master relay 19. The counter 18 is connected to the sensor 9 by means of a line carrying the voltage 14, and by means of a double relay 20 the master relay simultaneously stops the so-called "water time measurement" chronometer 21 and the so-called "total time measurement" chronometer 22. During the period required for preselection, the "water time" chronometer measures the cumulative passage time of the water drops, whilst the "total time" chronometer measures the period separating the first water pulse from the last one taken into account in the measurement.

Figure 5:
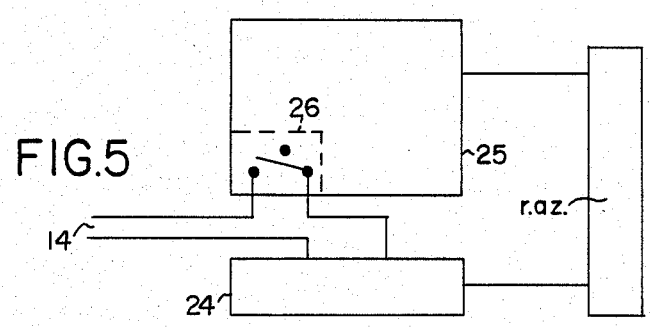
FIG. 5 is a general diagram of the means for evaluating the content of uncondensable substances according to a second method.

FIG. 5 shows the means for calculating by preselecting the total time; these means comprise a "water time" chronometer 24 and a programmable "total time" chronometer 25 incorporating a relay 26 which, at the end of programming, commands the stopping of the chronometer 24, the reading of which can give the required content directly.

Figure 6:
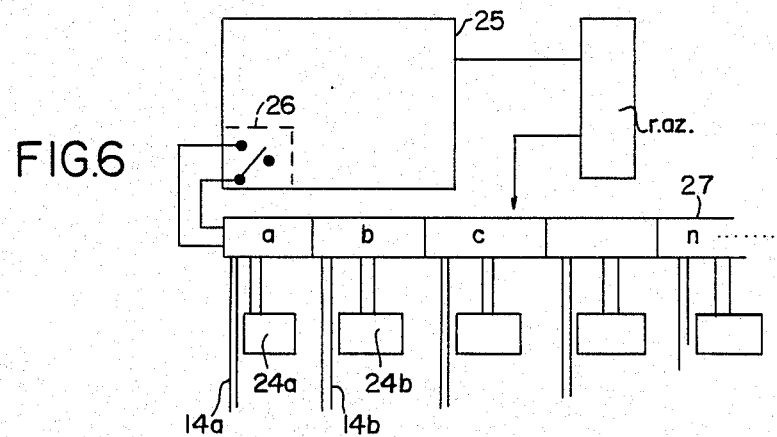
FIG. 6 is a general diagram of the means for evaluating the content of uncondensable substances according to a further method.

In FIG. 6, for n measuring channels in parallel, the chronometer 25 can be common to all of them, each channel only requiring a chronometer, such as 24. This is achieved by means of the master relay 26 which controls a multiple relay 27 for each channel.

These examples of methods are only given as an indication of the ways in which measurement can be achieved on the basis of the logical signal 14, and some functions can be performed by a microprocessor card.

Returning to FIG. 1, it will be noted that several "transmitter/measuring-tube/sensor" assemblies can be arranged in parallel downstream of a multi-channel peristaltic pump and connected either to as many calculators 17 or to a single calculator which senses each of the assemblies sequentially. In another way, because of the simplicity of an assembly comprising a condenser, a transmitter, a measuring tube, a sensor and a rectifier, a notch voltage 14 (FIG. 3) can be picked up at various points of a steam system and directed towards a single central calculator operating sequentially on the various points.

The present invention is employed in controlling the steam used in scraped-surface exchangers, controlling the steam generated by a boiler, controlling the bleeding of a cylinder drier, controlling the bleeding of an evaporator, especially a multiple-effect evaporator, controlling the mixing of the substances bled from a sterilizer, controlling the bleeding of an exchange-wall condenser, etc.

Although particular embodiments of the present invention have been described and/or illustrated, it must be understood, as regards both the measuring processes and the measuring devices, that the scope of the invention is not limited to these preferred embodiments, but extends to any other embodiment which conforms to the general definitions stated above.

We claim:

1. A device for measuring the content of an uncondensable substance in a gaseous mixture, the device comprising, in combination:
   means for obtaining a representative portion of the gaseous mixture;
   a condenser for receiving the representative portion and condensing the condensable substances therein, the condenser including a condenser tube of constant inside diameter sufficiently small to enable the isokinetic conveyance of gaseous bubbles and condensed droplets through said tube, the bubbles and droplets having meniscusses separating the same;
   a transparent measuring tube communicating with the condenser tube and having a refractive index at least approximately equal to that of the condensed droplets, the cross-sectional area of the measuring tube being not greater than that of the condenser tube and the diameter of the measuring tube being between about one and two millimeters; and
   an assembly including a light transmitter for directing a beam of light which intersects the measuring tube at a right angle and a photoelectric sensor for receiving the light beam, said light beam having a transverse dimension not less than the inside diameter of the measuring tube and being reflected by gaseous bubbles in the measuring tube but not by condensed droplets.

2. Device according to claim 1, characterized in that the transmitter transmits a beam of parallel light, the beam being of substantially cylindrical cross-section comparable to the inner cross-section of the measuring tube, so that the intersection of the beam and the measuring tube is approximately at a point.

3. Device according to claim 1, characterized in that the measuring tube is straight and of such a length that it contains alternate droplets and bubbles, and in that the beam has a highly flattened parallelipedic shape of thickness substantially equal to the diameter of the measuring tube, the mid-plane of the beam merging with the axis of the measuring tube, so that the intersection of the beam and the axis is approximately linear.

4. Process for evaluating the content of uncondensable substances present in a gaseous mixture, the said process using a device according to claim 1, characterized in that it involves conveying a succession of bubbles and droplets through the measuring tube at a substantially constant speed, measuring optically the respective lengths of the bubbles and droplets present in the measuring tube, and deducing the content of uncondensable substances present in the gaseous mixture from the ratio between the length of the bubbles and the lengths of the droplets.

5. Process according to claim 4, characterized in that the lengths of the bubbles and droplets are measured by measuring the time between the passages of the successive meniscusses separating the droplets from the bubbles, at a given point in the measuring tube.

6. Process according to claim 5, characterized in that the said time measurement is carried out with reference to a clock, the period of which is very small in relation to the passage time between two successive meniscusses.

7. Process according to claim 6, characterized in that the content of uncondensable substances is deduced from at least two of the measurements of the group of measurements which includes the cumulative measurement of the passage time of the droplets: tg, the cumulative measurement of the passage time of the bubbles: tb, and the cumulative measurement of the passage time of the droplets and bubbles: tt, these measurements being made on a reasonably numerous succession of droplets and bubbles, taking into account one of the ratios of the group of ratios including tb/tg, tb/tt, tg/tt and tttg/tt.

8. Process according to claim 7, characterized in that the total time is counted over a predetermined number of alternations.

9. Process according to claim 7, characterized in that the total time is counted over a predetermined period.

* * * * *